US012594401B2

(12) United States Patent　　　(10) Patent No.: US 12,594,401 B2

Xiao et al.　　　(45) Date of Patent: Apr. 7, 2026

(54) ADAPTER AND SURGICAL ASSISTANCE SYSTEM

(71) Applicant: ROBGENIX MEDICAL PTE. LTD., Singapore (SG)

(72) Inventors: Sa Xiao, Shanghai (CN); Hao Chen, Shanghai (CN); Cunwang Ge, Shanghai (CN); Gang Wu, Shanghai (CN)

(73) Assignee: ROBGENIX MEDICAL PTE. LTD., Singapore (SG)

( * ) Notice: Subject to any disclaimer, the term of this patent is extended or adjusted under 35 U.S.C. 154(b) by 0 days.

(21) Appl. No.: 19/052,243

(22) Filed: Feb. 12, 2025

(65) Prior Publication Data

US 2026/0048235 A1　　Feb. 19, 2026

Related U.S. Application Data

(63) Continuation of application No. PCT/CN2024/140575, filed on Dec. 19, 2024.

(30) Foreign Application Priority Data

Aug. 15, 2024　(CN) ......................... 202411126451.X

(51) Int. Cl.
*A61M 25/01*　　(2006.01)
*A61F 2/24*　　(2006.01)
*A61M 39/10*　　(2006.01)

(52) U.S. Cl.
CPC ........ *A61M 25/0113* (2013.01); *A61F 2/2436* (2013.01); *A61M 2039/1077* (2013.01); *A61M 2205/103* (2013.01)

(58) Field of Classification Search
None
See application file for complete search history.

(56) References Cited

U.S. PATENT DOCUMENTS

2002/0087166 A1　7/2002　Brock et al.
2015/0094732 A1*　4/2015　Pacheco ............. A61M 25/0113
606/108
(Continued)

FOREIGN PATENT DOCUMENTS

CN　108261256 A　7/2018
CN　111772706　10/2020
(Continued)

OTHER PUBLICATIONS

English machine translation of CN-115500948-A, Clarivate Analytics, 11 pages printed on May 12, 2025 (Year: 2025).*
(Continued)

*Primary Examiner* — Matthew Kremer
(74) *Attorney, Agent, or Firm* — Robert C. Kowert; Kowert, Hood, Munyon, Rankin & Goetzel, P.C.

(57) ABSTRACT

An adapter and a surgical assistance system are provided. The adapter includes a base including a bracket, a first input shaft and a second input shaft; a rotating base rotatably provided on the bracket and a rotating base transmission assembly including a first ring gear, where the first input shaft is in transmission connection with the first ring gear which is fixed with respect to the rotating base; and a catheter system drive assembly provided on the rotating base and a catheter system transmission assembly including a second ring gear and a planet gear, where the second input shaft is in transmission connection with the second ring gear, the second ring gear is in transmission connection with the planet gear, a shaft of the planet gear is fixed on the rotating base, and the planet gear is configured to drive the catheter system drive assembly. The adapter provided in the present disclosure can achieve two types of remote operations on the catheter system via two sets of relatively independent transmission assemblies, so as to improve the working environ- (Continued)

ment of medical staff and shorten the learning curve of doctors.

12 Claims, 8 Drawing Sheets

(56)                References Cited

U.S. PATENT DOCUMENTS

| | | | |
|---|---|---|---|
| 2017/0304015 | A1 | 10/2017 | Tavallaei et al. |
| 2024/0216089 | A1 | 7/2024 | Niikawa et al. |

FOREIGN PATENT DOCUMENTS

| | | | | |
|---|---|---|---|---|
| CN | 115500948 | A | * | 12/2022 |
| CN | 116262079 | A | | 6/2023 |
| CN | 117379233 | A | | 1/2024 |
| CN | 118267581 | A | | 7/2024 |
| CN | 221470692 | U | | 8/2024 |

OTHER PUBLICATIONS

Internation Search Report from PCT/CN2024/140575, dated Apr. 29, 2025, pp. 1-15 (includes English Translation).
Extended European Search Report from Application No. 24873871.8, Feb. 12, 2026, pp. 1-8.

* cited by examiner

102

103

ADAPTER AND SURGICAL ASSISTANCE SYSTEM

CROSS-REFERENCE TO RELATED APPLICATIONS

The present disclosure claims priority to Chinese patent application No. CN202411126451X, entitled "Adapter and Surgical Assistance System", filed on Aug. 15, 2024, which is incorporated herein by reference in its entirety.

TECHNICAL FIELD

The present disclosure relates to the technical field of medical devices, and particularly to an adapter and a surgical assistance system.

BACKGROUND

Currently, mitral regurgitation is typically treated by minimally invasive surgery. In particular, a valve repair device is delivered to a mitral valve of a patient by a catheter system and is operated remotely in vitro to repair the diseased mitral valve, thereby treating the mitral regurgitation. The catheter system is of a multi-layered structure, which has an outer sheath configured to penetrate the right atrium through a femoral vein and then pass through an interatrial septum to enter the left atrium so as to deliver the valve repair device to the mitral valve.

The use of the catheter system requires manual operations by a doctor, which are difficult and highly demanding in terms of technical skill and clinical experience, thereby causing a long learning curve for doctors and to some extent restricting the development of the surgical procedure or the clinical use of the devices. Moreover, during the surgical procedure, doctors mostly need to perform the surgery under the cooperation of CT (Computed Tomography) equipment, resulting in prolonged exposure of medical staff to a radiative environment, which can cause certain harm to the health of the medical staff. Therefore, it is necessary to provide a catheter adapter by which the catheter system can be remotely operated to improve the working environment for the medical staff and shorten the learning curve for doctors.

SUMMARY

As for the above problems in the prior art, an adapter and a surgical assistance system are provided, by which a catheter system can be remotely operated, and the working environment of the medical staff can be improved and a learning curve of doctors can be shortened.

The present disclosure provides the following solutions.

In a first aspect, the present disclosure provides an adapter including:

a base comprising a bracket, a first input shaft and a second input shaft;

a rotating base rotatably provided on the bracket and a rotating base transmission assembly including a first ring gear, where the first input shaft is in transmission connection with the first ring gear that is fixed with respect to the rotating base; and a catheter system drive assembly provided on the rotating base and a catheter system transmission assembly including a second ring gear and a planet gear, where the second input shaft is in transmission connection with the second ring gear, the second ring gear is in transmission connection with the planet gear, a shaft of the planet gear is fixed on the rotating base, and the planet gear is configured to drive the catheter system drive assembly.

In some possible embodiments, the first ring gear and the second ring gear are respectively provided on both sides of the bracket;

the first ring gear and the second ring gear are independent from each other.

In some possible embodiments, the rotating base transmission assembly further includes a first power input gear and a first transmission gear, and the first transmission gear includes a first gear portion and a second gear portion which are fixedly connected;

the first input shaft is sleeved with a first power input gear that is engaged with the first gear portion, and the second gear portion is engaged with the first ring gear.

In some possible embodiments, the first gear portion is connected to the second gear portion via a first gear shaft that passes through the bracket, and the first gear portion and the second gear portion are respectively located on both sides of the bracket.

In some possible embodiments, the second ring gear includes an outer ring gear and an inner ring gear which are fixed relative to each other, the second input shaft is in transmission connection with the outer ring gear, and the inner ring gear is engaged with the planet gear.

In some possible embodiments, the catheter system transmission assembly further includes a flexible transmission assembly;

the planet gear is connected to the catheter system drive assembly via the flexible transmission assembly.

In some possible embodiments, the catheter system transmission assembly further includes a second power input gear and a second transmission gear which includes a third gear portion and a fourth gear portion which are fixedly connected;

the second input shaft is sleeved with a second power input gear that is engaged with the third gear portion, and the fourth gear portion is engaged with the outer ring gear.

In some possible embodiments, the third gear portion is connected to the fourth gear portion via a second gear shaft, the second gear shaft passes through the bracket, and the third gear portion and the fourth gear portion are located on the same side of the bracket.

In some possible embodiments, the catheter system includes an outer catheter unit, a middle catheter unit and an inner catheter unit, the outer catheter unit is mounted to the rotating base, and the catheter system drive assembly is configured to drive a knob of the outer catheter unit.

In some possible embodiments, a first channel provided in the bracket and a second channel provided in the rotating base form a hollow structure of the adapter;

the hollow structure is configured to accommodate the outer catheter unit.

In some possible embodiments, the adapter further includes a housing provided on a side of the second ring gear away from the base;

the housing further includes a fixed screw, the housing is provided with a first fixed hole, the bracket is provided with a second fixed hole, an adapter transmission device corresponding to the adapter is provided with a threaded hole, and the fixed screw is configured to fix the adapter on the adapter transmission device via the first fixed hole, the second fixed hole and the threaded hole;

the adapter transmission device is configured to drive the first input shaft and the second input shaft.

In some possible embodiments, the threaded hole is provided with a first thread;

a first portion of a screw rod of the fixed screw close to a nut of the fixed screw is smooth, and a second portion of the screw rod away from the nut is provided with a second thread matching with the first thread;

an outer diameter of the first portion of the screw rod is smaller than or equal to the minimum inner diameter of the first fixed hole, an outer diameter of the second portion of the screw rod is greater than the minimum inner diameter of the first fixed hole, and the outer diameter of the second portion of the screw rod is smaller than or equal to the inner diameter of the second fixed hole.

In some possible embodiments, the first fixed hole includes a first through hole and a second through hole which are axially connected, and the first through hole is provided on a side away from the second fixed hole;

the inner diameter of the first through hole is equal to or larger than the outer diameter of the first portion of the screw rod, the inner diameter of the first through hole is smaller than the outer diameter of the second portion of the screw rod, and the inner diameter of the second through hole is larger than or equal to the outer diameter of the second portion of the screw rod.

In a second aspect, the embodiments of the present disclosure provide a surgical assistance system including an adapter transmission device configured to drive a first input shaft and a second input shaft of the adapter separately, and an adapter as described above.

The adapter provided by the embodiments of the present disclosure can operate the rotating base to rotate via the rotating base and the rotating base transmission assembly to cause the rotation of the catheter system; the assembly in the catheter system can be driven by the catheter system drive assembly and the catheter system transmission assembly such that the catheter system can perform a corresponding action. The adapter provided by the embodiments of the present disclosure can achieve two types of remote operations on the catheter system via two sets of relatively independent transmission assemblies, so as to improve the working environment of medical staff and shorten a learning curve of doctors.

Other advantages of the present disclosure will be explained in more detail in conjunction with the following description and the accompanying drawings.

It should be understood that the above description is only an overview of the technical solutions of the present disclosure, so that the technical means of the present disclosure can be more clearly understood, and thus can be implemented according to the description. In order that the above and other objectives, features, and advantages of the present disclosure can be more readily understood, the following detailed description of the present disclosure is set forth.

BRIEF DESCRIPTION OF DRAWINGS

Advantages and benefits described herein, as well as other advantages and benefits, will become apparent to a person skilled in the art upon reading the following detailed description of exemplary embodiments. The drawings are only for purposes of illustrating exemplary embodiments and are not to be construed as limiting the present disclosure. Furthermore, the same reference numerals designate the same components throughout the drawings. In the drawings.

Figure 1:
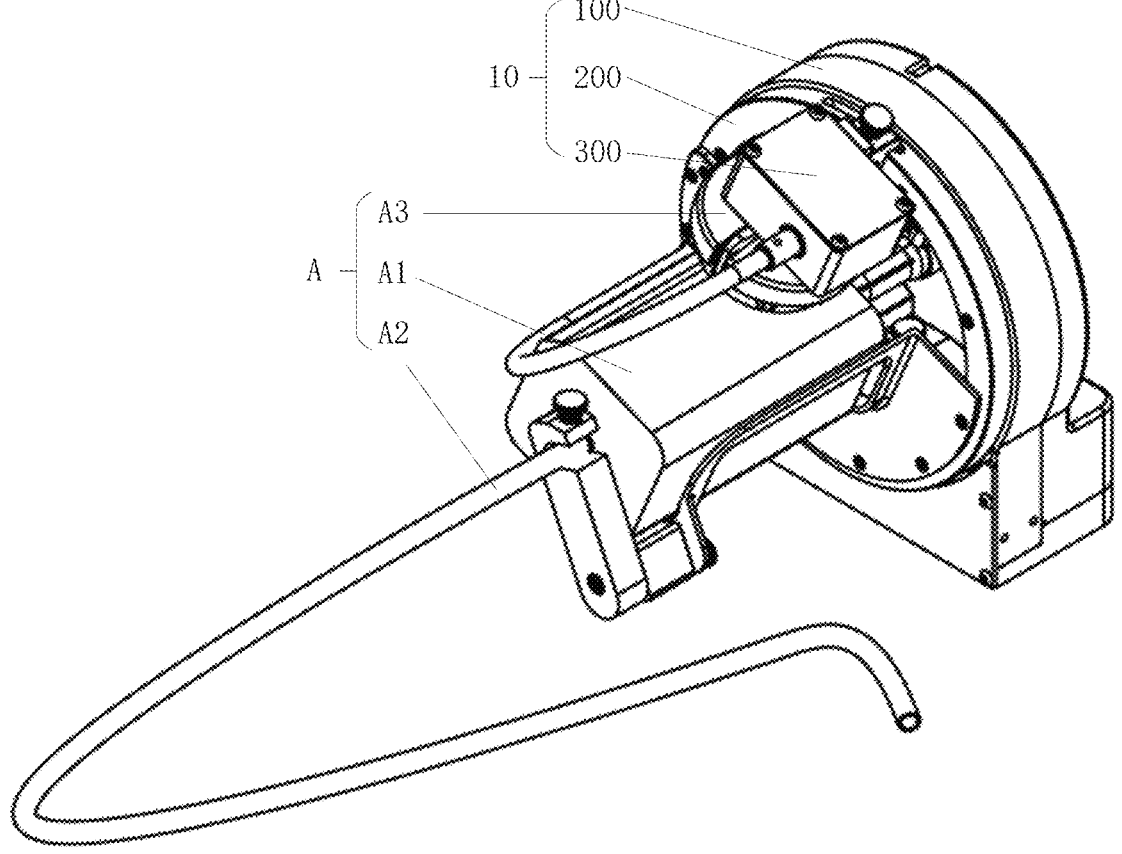
FIG. 1 is an assembled schematic diagram illustrating an adapter and an outer catheter unit according to an embodiment of the present disclosure.

In the drawings, the components identified by the reference numerals are listed as follows:

base 100; bracket 101; first input shaft 102; second input shaft 103; rotating base 200; first ring gear 201; first retainer ring 211; first power input gear 202; first transmission gear 203; first gear portion 213; second gear portion 223; first gear shaft 233; catheter system drive assembly 300; second ring gear 301; outer ring gear 311; inner ring gear 321; second retainer ring 331; planet gear 302; second power input gear 303; second transmission gear 304; third gear portion 314; fourth gear portion 324; second gear shaft 334; flexible transmission assembly 305; housing 400; fixed screw 401; first portion of screw rod 411; second portion of screw rod 421; first fixed hole 402; first through hole 412; second through hole 422; outer catheter unit A; handle A1; sheath A2; knob A3; connector A4.

In the drawings, the same or corresponding reference numerals denote the same or corresponding parts.

DETAILED DESCRIPTION

Exemplary embodiments of the present disclosure will be described in more detail below referring to the accompanying drawings. While the exemplary embodiments of the present disclosure are shown in the drawings, it should be understood that the present disclosure may be embodied in various forms and should not be limited to the embodiments set forth herein. Rather, these embodiments are provided so that the present disclosure will be understood more thoroughly, and will fully convey the scope of the present disclosure to a person skilled in the art.

In the description of the embodiments of the present disclosure, it should be understood that terms such as "including" or "having" are intended to indicate the presence of the disclosed features, numerals, steps, actions, components, parts, or combinations thereof in the specification, and do not exclude the possibility of the presence of one or more other features, numerals, steps, actions, components, parts, or combinations thereof. The terms "first", "second" and the like are used for distinguishing between similar or identical features for convenience of description only and are not to be construed as indicating or implying a relative importance or number of such features. Thus, a feature defined by "first", "second", etc. may explicitly or implicitly include one or more of such features. In the description of the embodiments of the present disclosure, unless otherwise specified, the term "a plurality of" means two or more than two.

"/" means, unless otherwise stated, for example, A/B may represent A or B; as used herein, "and/or" is merely an association relationship describing an associated object, meaning that there may be three relationships, e.g., A and/or B, which may mean: there are three cases of A alone, A and B together, and B alone. For ease of description, spatial relationship terms such as "below", "under", "above", "on", and the like may be used herein to describe one element or feature's relationship to other elements or features illustrated in the figures. It will be understood that the spatial relationship terms are intended to encompass other orientations of the device in use or operation in addition to the orientation depicted in the accompanying drawings.

In addition, it should be noted that the embodiments and features of the embodiments in the present disclosure can be combined with each other without conflict. The present disclosure will now be described in detail in connection with the embodiments referring to the accompanying drawings.

As an assistance equipment commonly used in minimally invasive surgery, the delivery system is mainly used to deliver an interventional therapy device into the body of a patient for the purpose of treatment, for example, a valve repair device is delivered to the mitral valve or tricuspid valve of the patient and operated remotely in vitro to repair the diseased mitral valve or tricuspid valve; as another example, a bracket is delivered into the blood vessel of the patient to treat vascular stenosis, etc. The delivery system includes at least one sheath system which typically includes a sheath and an operating means, such as a handle, connected to a proximal end of the sheath to control the movement of the sheath.

For a delivery system for delivering a mitral valve repair device, the delivery system may include an outer sheath unit, a middle sheath unit, and an inner sheath unit. The outer sheath unit includes an outer sheath which is required to enter the right atrium along the femoral vein. After the outer sheath is bent, orientation of an end of the outer sheath is adjusted by rotating the outer sheath to ensure that the outer sheath can face the atrial septum, so that the outer sheath can penetrate the atrial septum under the guidance of the guide wire and enter the left atrium. The middle sheath unit includes a middle sheath, where the middle sheath is provided through the outer sheath and can extend from the end of the outer sheath, a extending portion of the middle sheath can bend left and right in a first plane and can also bend left and right in a second plane, and the first plane and the second plane are provided at an angle to each other. When the outer sheath reaches the left atrium, the middle sheath extends through the outer sheath into the left atrium, and during the movement of the middle sheath relative to the outer sheath, the bending direction and bending degree of the middle sheath in the first plane and the second plane according to the bending direction and bending degree of the outer sheath need to be adjusted in real time, so that the middle sheath can reach the appropriate position. The inner sheath unit includes an inner sheath that is inserted through the middle sheath and can extend from an end of the middle sheath, where an end of the inner sheath is detachably connected to the valve repair device, the inner sheath can extend through the middle sheath into the left atrium, and then the inner sheath is bent towards the position of the mitral valve and extends towards the mitral valve, thereby delivering the valve repair device to the mitral valve.

Taking the above outer sheath unit as an example, as shown in FIG. 1, the adapter 10 provided by the embodiments of the present disclosure can be configured to control an outer catheter unit A, where the outer catheter unit A includes a handle A1, a sheath A2 and a knob A3, where the proximal end of the sheath A2 is provided on the handle A1, and the knob A3 is provided on the handle A1 and configured to drive the sheath A2 to bend. The adapter 10 includes a base 100, a rotating base 200, and a catheter system drive assembly 300. The rotating base 200 of the adapter 10 is configured to cause the rotation of the whole outer catheter unit A of the handle A1, and the catheter system drive assembly 300 is configured to cause the rotation of the knob A3 of the outer catheter unit A.

Reference will now be made in detail to an adapter 10 provided by the embodiments of the present disclosure, referring to FIG. 1, FIG. 1 is a schematic diagram illustrating an adapter provided by the embodiments of the present disclosure.

Figure 2:
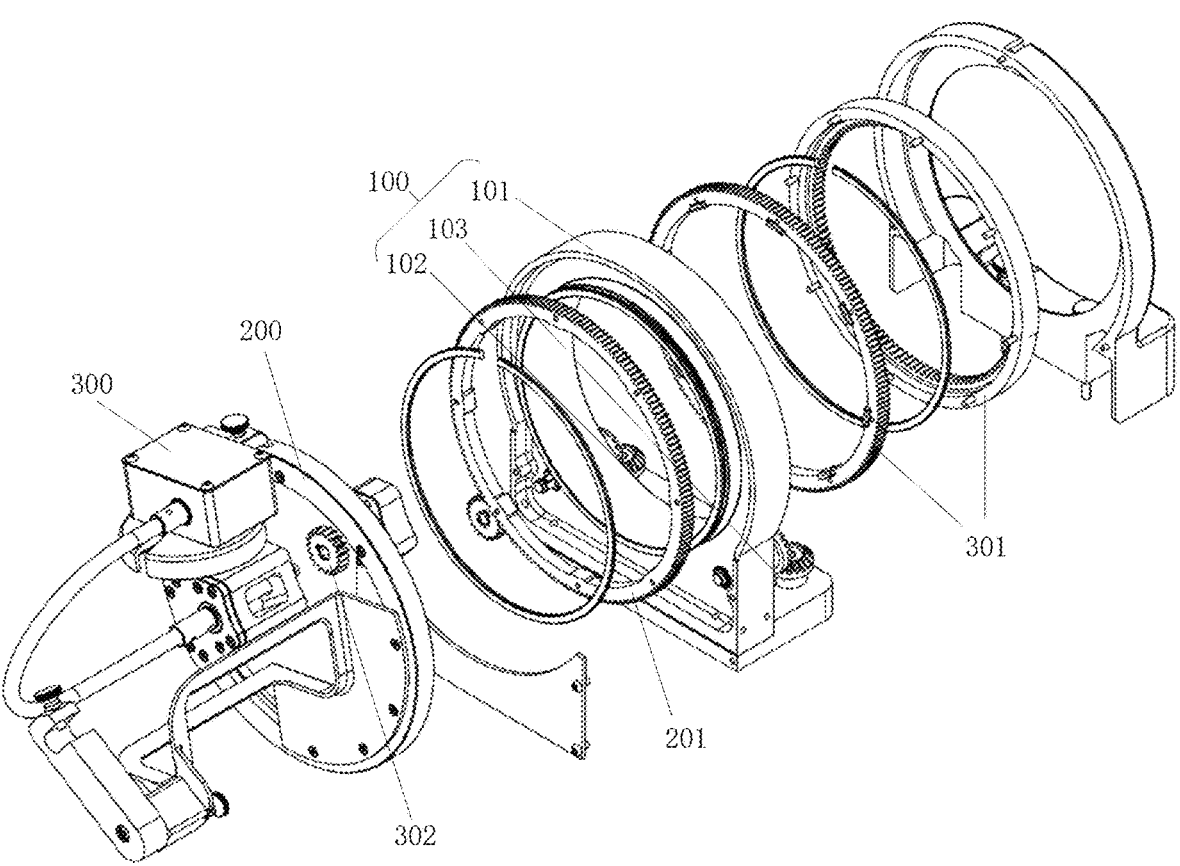
FIG. 2 is a schematic exploded view of an adapter according to an embodiment of the present disclosure.

As shown in FIG. 2, an adapter provided by the embodiments of the present disclosure includes:

a base 100 including a bracket 101, a first input shaft 102 and a second input shaft 103;

a rotating base 200 rotatably provided on the bracket 101 and a rotating base transmission assembly including a first ring gear 201, where the first input shaft 102 is in transmission connection with the first ring gear 201 that is fixed with respect to the rotating base 200;

a catheter system drive assembly 300 and a catheter system transmission assembly, where the catheter system drive assembly 300 is provided on the rotating base 200, the catheter system transmission assembly includes a second ring gear 301 and a planet gear 302, the second input shaft 103 is in transmission connection with the second ring gear 301, the second ring gear 301 is in transmission connection with the planet gear 302, a shaft of the planet gear 302 is fixed on the rotating base 200, and the planet gear 302 is configured to drive the catheter system drive assembly 300.

It can be seen therefrom that the adapter provided by the embodiments of the present disclosure can operate the rotating base to rotate via the rotating base and the rotating base transmission assembly to cause the rotation of the catheter system; the assembly in the catheter system can be driven by the catheter system drive assembly and the catheter system transmission assembly such that the catheter system can perform a corresponding action. The adapter provided by the embodiments of the present disclosure can achieve two types of remote operations on the catheter system via two sets of relatively independent transmission assemblies, so as to improve the working environment of medical staff and shorten a learning curve of doctors.

In order to make the catheter system transmission assembly and the rotating base transmission assembly more independent, that is, they do not interfere with each other during operation. The first ring gear 201 and the second ring gear 301 in the embodiments of the present disclosure may be respectively provided on both sides of the bracket 101, so that the first ring gear 201 and the second ring gear 301 are independent from each other and do not interfere with each other at any relative position.

Figure 3:
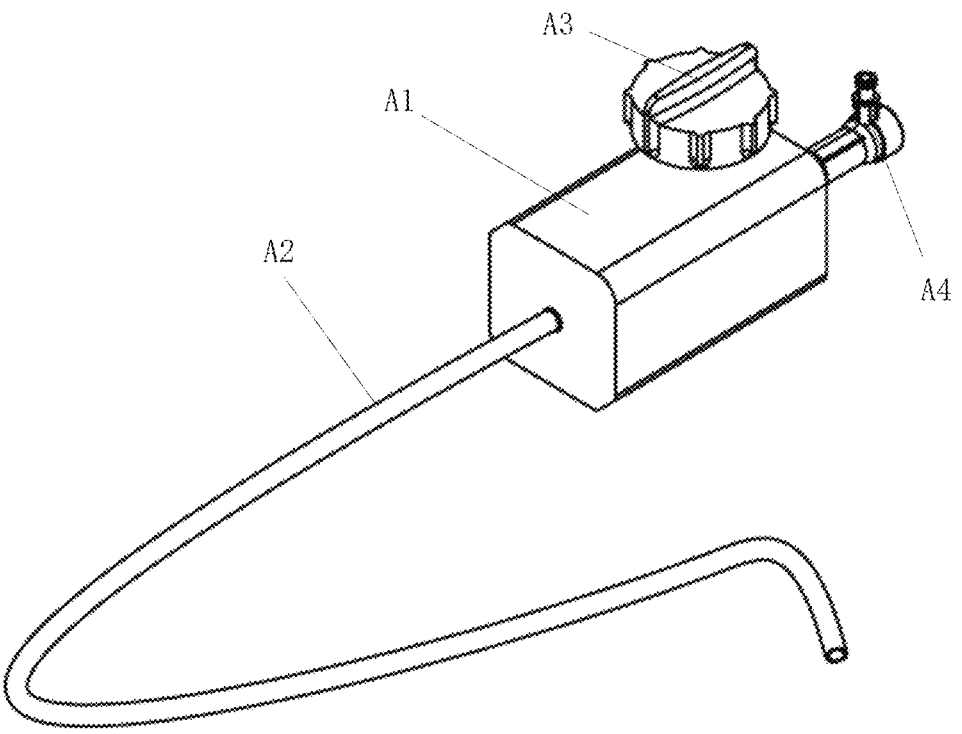
FIG. 3 is a schematic diagram illustrating an outer catheter unit according to an embodiment of the present disclosure.

As shown in FIG. 2, a first channel provided in the bracket 101 and a second channel provided in the rotating base 200 form a hollow structure of the adapter 10. The hollow structure serves to accommodate the outer catheter unit A. As shown in FIG. 3, the outer catheter unit A further includes a connector A4. The connector A4 may be a Luer connector.

The connector A4 is used to connect an extension tube, a connector, a syringe or other medical devices, and is located within the hollow structure of the adapter 10 when the outer catheter unit A is mounted to adapter 10. Thus, if the diameter of the hollow structure is small, the connection of the extension tube, the connector, the syringe or other medical devices to the outer catheter unit A will be restricted. The first ring gear 201, the second ring gear 301 and the bracket 100 in the embodiments of the present disclosure can cooperate to form a through hole with a larger diameter to facilitate the installation of the extension tube, the connector, the syringe or other medical devices with the adapter 10 during use.

Figure 4:
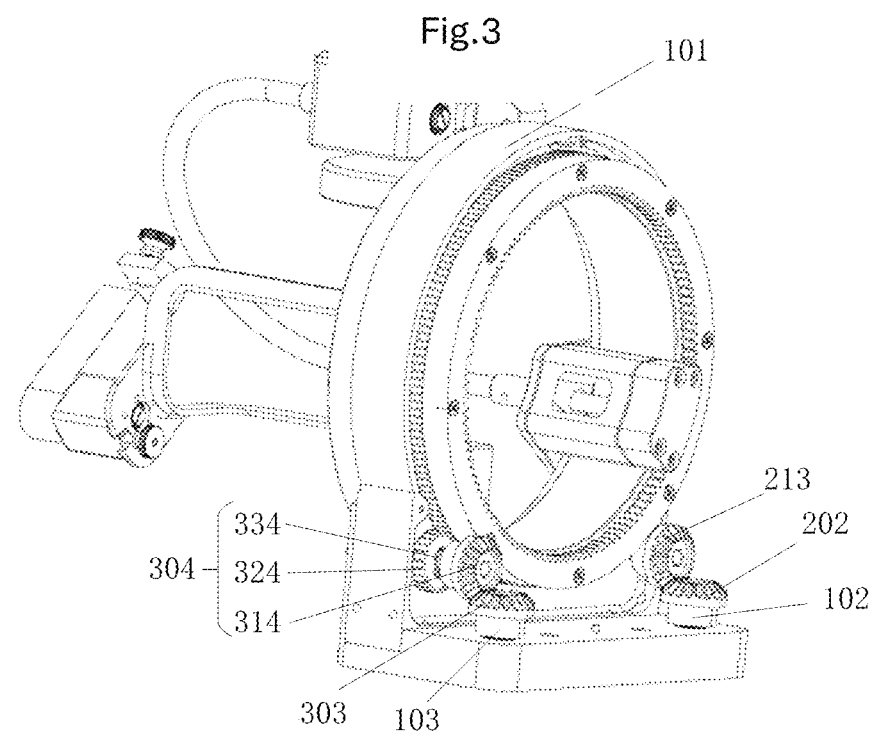
FIG. 4 is a schematic diagram illustrating an adapter according to an embodiment of the present disclosure.
Figure 5:
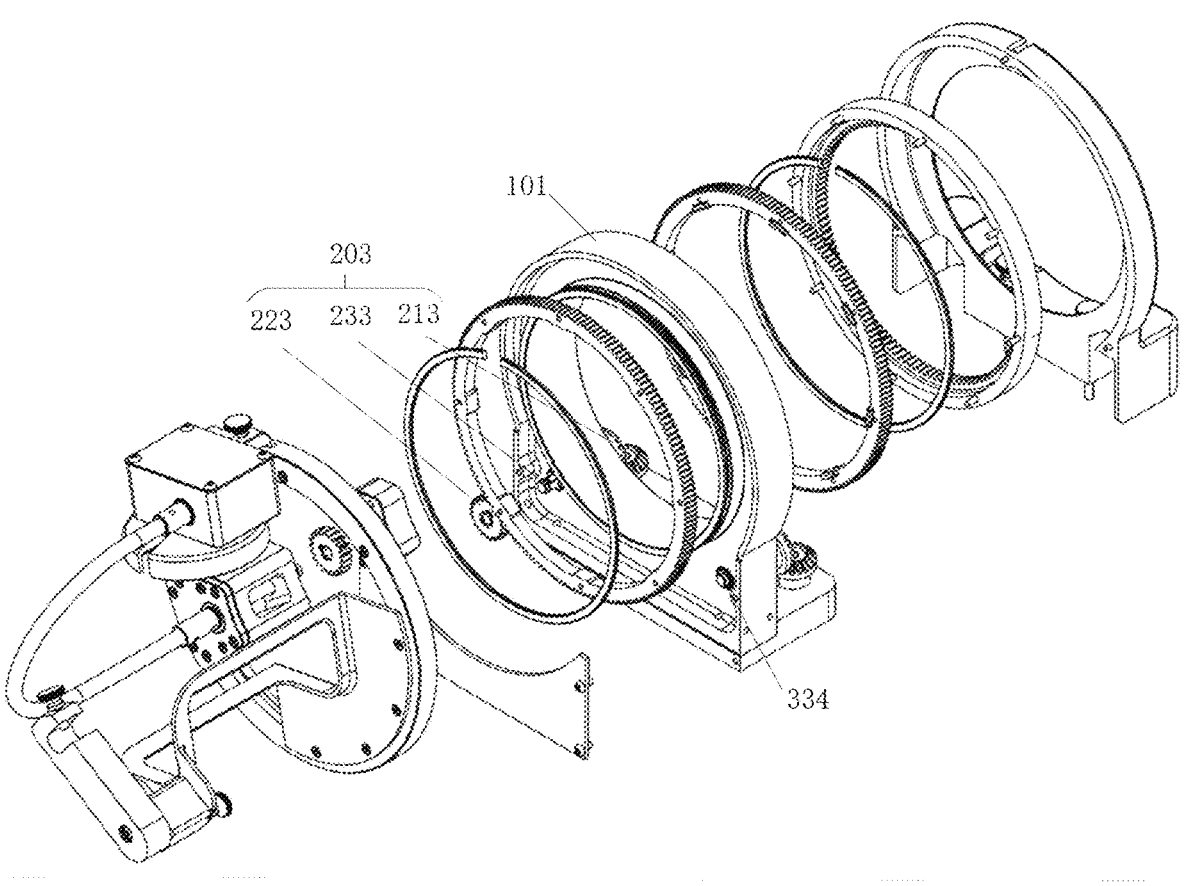
FIG. 5 is a schematic exploded view of an adapter according to an embodiment of the present disclosure.

As shown in FIGS. 4 and 5, the rotating base transmission assembly in the embodiments of the present disclosure may further include a first power input gear 202 and a first transmission gear 203, the first transmission gear 203 includes a first gear portion 213 and a second gear portion 223 fixedly connected. The first input shaft 102 is sleeved with the first power input gear 202 that is engaged with the first gear portion 213 and the second gear portion 223 that is engaged with the first ring gear 201. The first gear portion 213 is connected to the second gear portion 223 via a first gear shaft 233 that passes through the bracket 101, and the first gear portion 213 and the second gear portion 223 are respectively located on both sides of the bracket 101.

As shown in FIGS. 4 and 5, the catheter system transmission assembly further includes a second power input gear 303 and a second transmission gear 304 which includes a third gear portion 314 and a fourth gear portion 324 which are fixedly connected. The second input shaft 103 is sleeved with a second power input gear 303 that is engaged with the third gear portion 314. The third gear portion 314 is connected to the fourth gear portion 324 via a second gear shaft 334 which passes through the bracket 101, and the third gear portion 314 and the fourth gear portion 324 are located on the same side of the bracket 101.

Figure 6:
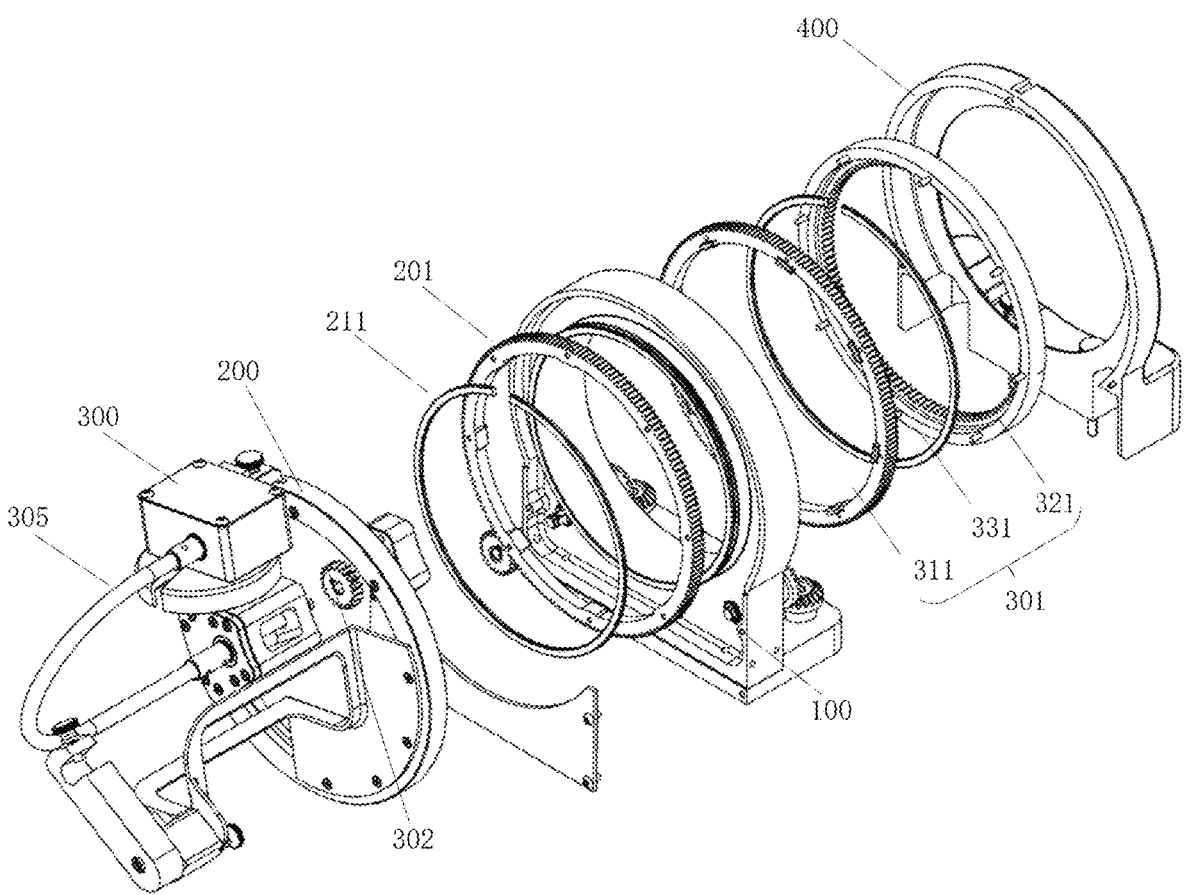
FIG. 6 is a schematic exploded view of another adapter according to an embodiment of the present disclosure.

As shown in FIG. 6, the first ring gear 201 may be an outer ring gear. The first ring gear 201 is fixedly connected to the rotating base 200 in an axial direction. The rotating base 200 may be provided with a radial protrusion structure, and the first ring gear 201 is provided with a hole that matches the protrusion structure on the rotating base 200. The first ring gear 201 is fixedly connected to the rotating base 200 to rotate in synchronization with the matched protrusion structure and the hole. The first ring gear 201 and the rotating base 200 may be provided with a first retainer ring 211 for enhancing the stability of the connection between the first ring gear 201 and the rotating base 200.

As shown in FIG. 6, the second ring gear 301 provided by the embodiments of the present disclosure may include an outer ring gear 311, an inner ring gear 321, and a second retainer ring 331 which are fixed relative to each other. The outer ring gear 311 is fixedly connected to the inner ring gear 321 in the axial direction. The outer ring gear 311 may be provided with a radially protrusion structure, the inner ring gear 321 is provided with a hole matching the protrusion structure on the outer ring gear 311, and the inner ring gear 321 and the outer ring gear 311 are fixedly connected and rotate synchronously via the matched protrusion structure and the hole. The second retainer ring 331 is provided between the inner ring gear 321 and the outer ring gear 311 and is used for enhancing structural stability of the second ring gear 301.

As one possible implementation, the second input shaft 103 in the embodiments of the present disclosure may be in transmission connection with the outer ring gear 311, in particular, the fourth gear portion 324 may be engaged with the outer ring gear 311. The ring gear 321 may be in transmission connection with the catheter system drive assembly 300, in particular, the ring gear 321 may be engaged with the planet gear 302. In practice, as shown in FIG. 6, the catheter system transmission assembly provided by the embodiments of the present disclosure may further include a flexible transmission assembly 305. The planet gear 302 may be connected to the catheter system drive assembly 300 via the flexible transmission assembly 305.

Figure 7:
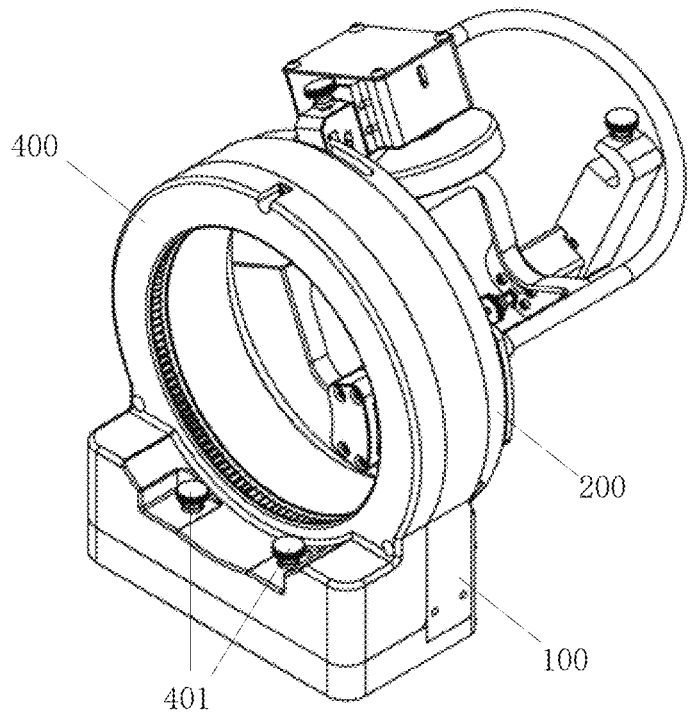
FIG. 7 is a schematic diagram illustrating an adapter according to an embodiment of the present disclosure.

As shown in FIGS. 6 and 7, the adapter provided by the embodiments of the present disclosure further includes a housing 400. The housing 400 is provided on a side of the second ring gear 301 away from the base 100; the housing 400 further includes a fixed screw 401, the housing 400 is provided with a first fixed hole, the base 100 is provided with a second fixed hole, an adapter transmission device corresponding to the adapter is provided with a threaded hole, and the fixed screw 401 is configured to fix the adapter on the adapter transmission device via the first fixed hole, the second fixed hole and the threaded hole; the adapter transmission device is configured to drive the first input shaft and the second input shaft.

Figure 8:
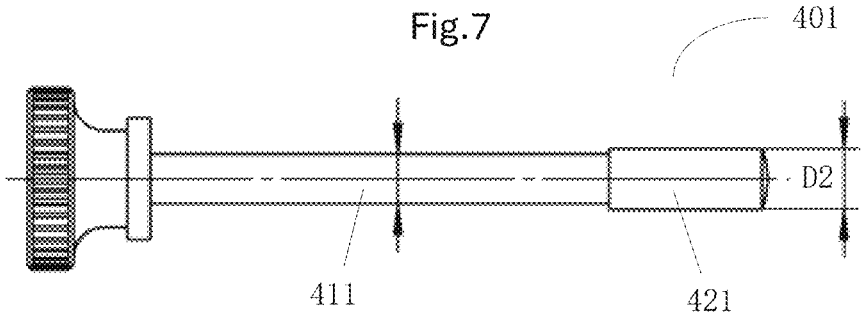
FIG. 8 is a schematic diagram illustrating a fixed screw according to an embodiment of the present disclosure.
Figure 9:
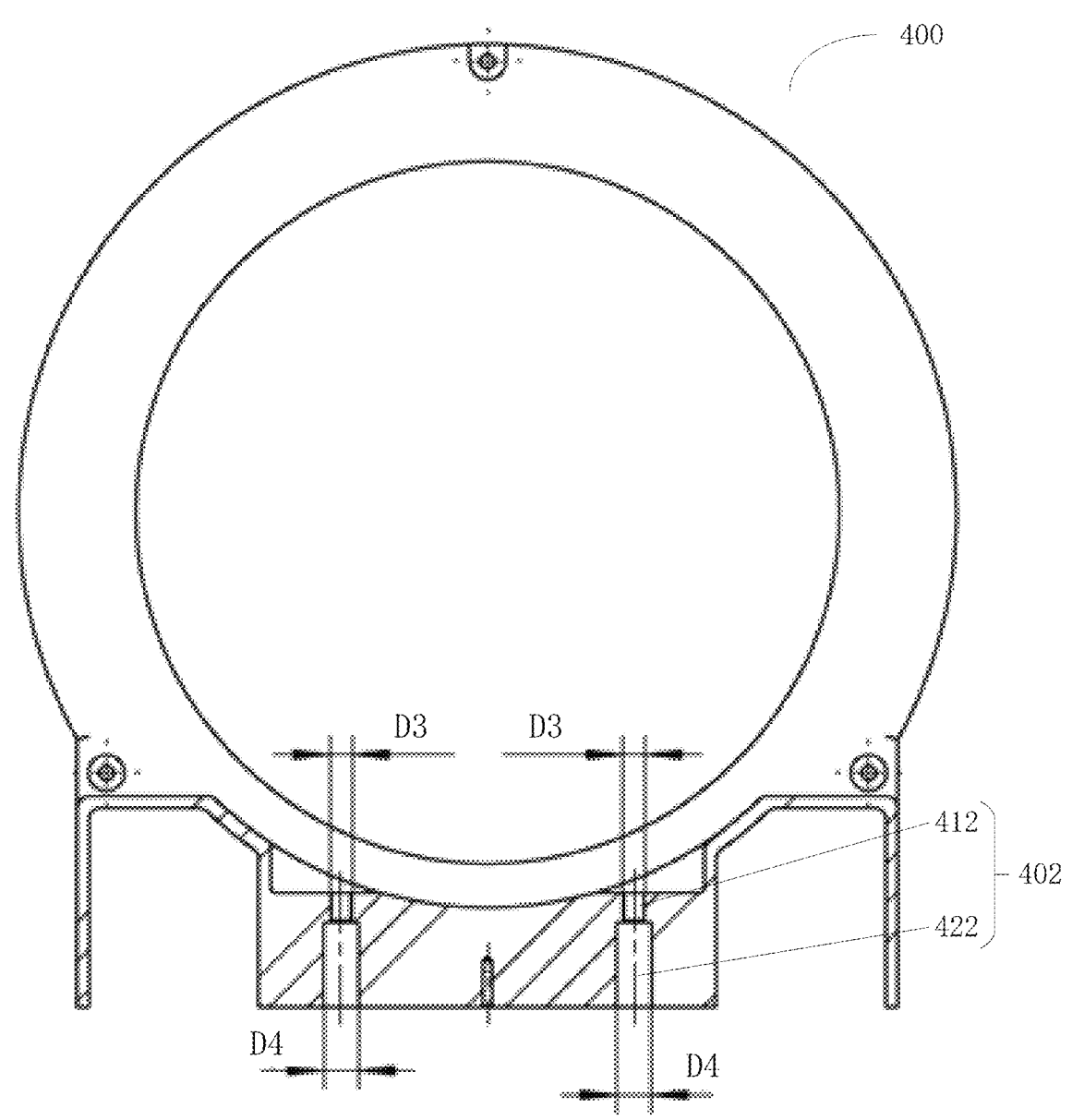
FIG. 9 is a schematic diagram illustrating a housing according to an embodiment of the present disclosure.

The threaded hole of the adapter rotating device in the embodiments of the present disclosure may be provided with a first thread. As shown in FIGS. 8 and 9, a first portion 411 of the screw rod of the fixed screw 401 close to the nut of the fixed screw 401 is smooth, and a second portion 421 of the screw rod away from the nut is provided with a second thread matching with the first thread. In practice, the outer diameter D1 of the first portion 411 of the screw rod is smaller than or equal to the minimum inner diameter D3 of the first fixed hole 402, the outer diameter D2 of the second portion 421 of the screw rod is greater than the minimum inner diameter D3 of the first fixed hole 402, and the length of the first portion 411 of the screw rod is greater than the corresponding axial length of the minimum inner diameter portion of the first fixed hole 402. The outer diameter D2 of the second portion 421 of the screw rod is smaller than or equal to the inner diameter of the second fixed hole. When the adapter provided by the present disclosure leaves the factory, the first portion 411 of the screw rod can be directly stuck in the first fixed hole 402, and since the outer diameter D2 of the second portion 421 of the screw rod is greater than the minimum inner diameter D3 of the first fixed hole 402, the fixed screw 401 cannot be dislodged from the first fixed hole 402. As such, the embodiments of the present disclosure provide a fixed screw that reduces packaging complexity while eliminating the risk of the fixed screw being lost, and that avoids the fixing screw falling off during replacement or assembly of the fixed screw adapter, resulting in secondary contamination of the fixed screw, thereby improving convenience of use.

As one possible embodiment, as shown in FIG. 9, the first fixed hole 402 includes a first through hole 412 and a second through hole 422 connected in an axial direction, the first through hole 412 is provided on a side away from the second fixed hole; the inner diameter D3 of the first through hole 412 is equal to or larger than the outer diameter D1 of the first portion 411 of the screw rod, the inner diameter D3 of the first through hole 412 is smaller than the outer diameter D2 of the second portion 421 of the screw rod, and the inner diameter D4 of the second through hole 422 is larger than or equal to the outer diameter D2 of the second portion 421 of the screw rod. Thus, the first portion 411 of the screw rod can be directly stuck in the first through hole 412, and since the outer diameter D2 of the second portion 421 of the screw rod is larger than the inner diameter D3 of the first through hole 412, the fixed screw 401 cannot be dislodged from the first fixed hole 402. As such, the embodiments of the present disclosure provide a fixed screw that reduces packaging complexity while eliminating the risk of the fixed screw being lost, and that avoids the fixing screw falling off during replacement or assembly of the fixed screw adapter, resulting in secondary contamination of the fixed screw, thereby improving convenience of use.

In summary, the adapter provided by the embodiments of the present disclosure achieve two types of remote operations on the catheter system via two sets of relatively independent transmission assemblies, so as to improve the working environment of medical staff and shorten a learning curve of doctors; the adaptability of the catheter system to the difference in the size of medical devices is increased by the arrangement of the large-sized hollow structure in the adapter; further, secondary contamination of the fixed screw caused by the falling off of the fixed screw from the adapter is avoided by the design of the fixed screw.

Figure 10:
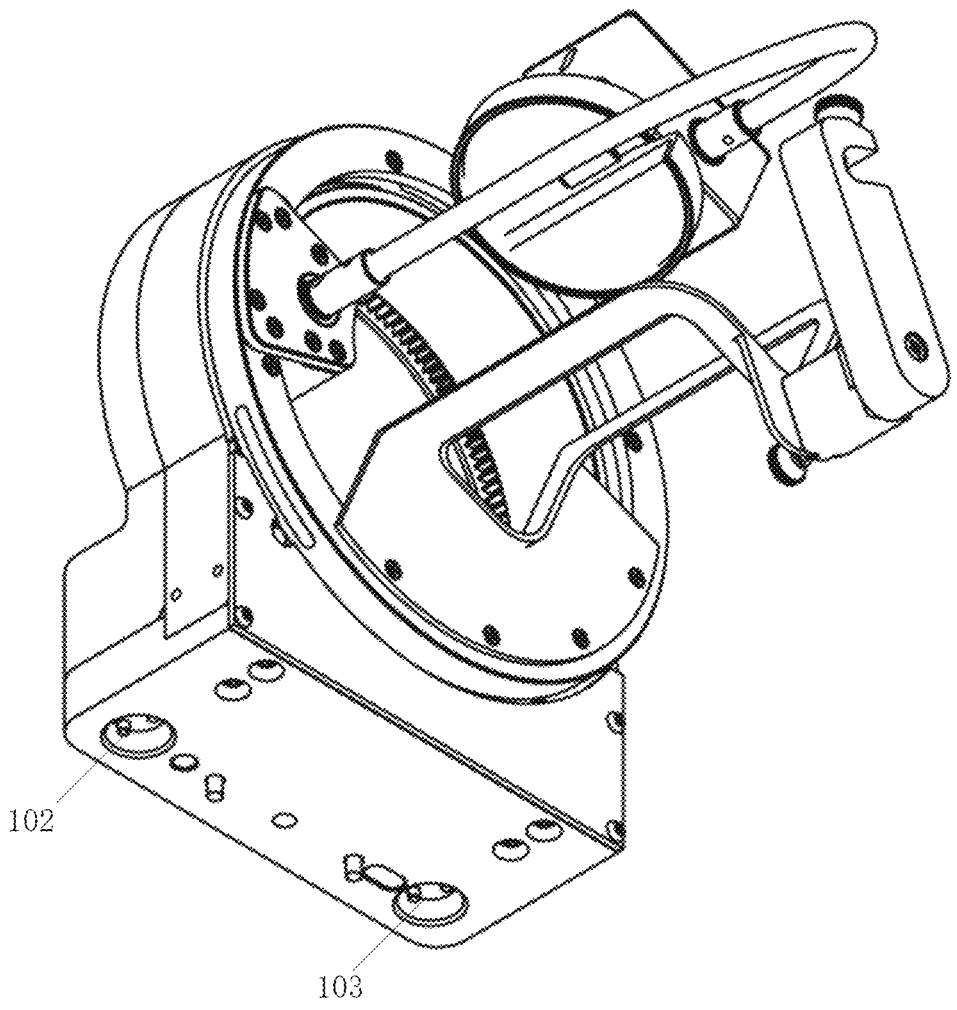
FIG. 10 is a schematic diagram illustrating an adapter according to an embodiment of the present disclosure.

According to the adapter provided by the above embodiments, the present disclosure also provides a surgical assistance system. The embodiments of the present disclosure provide a surgical assistance system including an adapter transmission device and an adapter as in the above embodiments. As shown in FIG. 10, the adapter transmission device is configured to drive a first input shaft 102 and a second input shaft 103 of the adapter separately.

It should be noted that the surgical assistance system of the embodiments of the present disclosure may include various components of the above embodiments of the adapter to achieve the same effects and functions, which will not be described in detail herein.

While illustrative embodiments of the present disclosure have been illustrated and described in detail in the drawings and foregoing description, they are to be considered as illustrative and not restrictive, it should be understood that only certain illustrative embodiments have been shown and described and that all changes and modifications that are desired to be protected within the spirit of the present disclosure as claimed are intended to be covered. It should be understood that although the words such as preferred, preferable, more preferable or most preferable are used in the above description to indicate that the described features may be more desirable, they may not be necessary and it can be conceived that embodiments without these features are within the scope of the present disclosure, which is defined by the appended claims. When reading the claims, the use of words such as "a," "an," "at least one," or "at least one portion" does not intend to limit the claims to only one, unless specifically stated otherwise in the claims. When using the language "at least a portion" and/or "a portion", the item may include a portion and/or the whole item, unless there is a specific contrary indication.

Although the spirit and principles of the present disclosure have been described with reference to several specific embodiments above, it should be understood that the present disclosure is not limited to the disclosed specific embodiments, and the division of various aspects does not mean that the features in these aspects cannot be combined. The present disclosure is intended to cover various modifications and equivalent arrangements within the spirit and scope of the appended claims.

What is claimed is:

1. An adapter comprising:
   a base comprising a bracket, a first input shaft and a second input shaft;
   a rotating base rotatably provided on the bracket;
   a rotating base transmission assembly comprising a first ring gear, wherein the first input shaft is in transmission connection with the first ring gear that is fixed with respect to the rotating base;
   a catheter system drive assembly provided on the rotating base; and
   a catheter system transmission assembly comprising a second ring gear and a planet gear, wherein the second input shaft is in transmission connection with the second ring gear, the second ring gear is in transmission connection with the planet gear, a shaft of the planet gear is fixed on the rotating base, and the planet gear is configured to drive the catheter system drive assembly,
   wherein the rotating base transmission assembly further comprises a first power input gear and a first transmission gear, and the first transmission gear comprises a first gear portion and a second gear portion fixedly connected to each other;
   wherein the first input shaft is sleeved with the first power input gear that is engaged with the first gear portion, and the second gear portion is engaged with the first ring gear, and
   wherein the first gear portion is connected to the second gear portion via a first gear shaft that passes through the bracket, and the first gear portion and the second gear portion are respectively located on both sides of the bracket.

2. The adapter according to claim 1, wherein the first ring gear and the second ring gear are respectively provided on both sides of the bracket; and
   the first ring gear and the second ring gear are independent from each other.

3. The adapter according to claim 1, wherein the second ring gear comprises an outer ring gear and an inner ring gear which are fixed relative to each other, the second input shaft is in transmission connection with the outer ring gear, and the inner ring gear is engaged with the planet gear.

4. The adapter according to claim 3, wherein the catheter system transmission assembly further comprises a flexible transmission assembly;
   the planet gear is connected to the catheter system drive assembly via the flexible transmission assembly.

5. The adapter according to claim 3, wherein the catheter system transmission assembly further comprises a second power input gear and a second transmission gear, and the second transmission gear comprises a third gear portion and a fourth gear portion fixedly connected to each other;
   the second input shaft is sleeved with the second power input gear that is engaged with the third gear portion, and the fourth gear portion is engaged with the outer ring gear.

6. The adapter according to claim 5, wherein the third gear portion is connected to the fourth gear portion via a second gear shaft,
   the second gear shaft passes through the bracket, and the third gear portion and the fourth gear portion are located on the same side of the bracket.

7. The adapter according to claim 1, further configured to control a catheter system comprising an outer catheter unit, a middle catheter unit and an inner catheter unit, wherein the outer catheter unit is mounted to the rotating base, and the catheter system drive assembly is configured to drive a knob of the outer catheter unit.

8. The adapter according to claim 7, wherein a first channel provided in the bracket and a second channel provided in the rotating base form a hollow structure of the adapter;

the hollow structure is configured to accommodate the outer catheter unit.

9. The adapter according to claim 1, further comprising a housing provided on a side of the second ring gear away from the base;

the housing comprises a fixed screw, the housing is provided with a first fixed hole, the bracket is provided with a second fixed hole, and the fixed screw is configured to fix the adapter on an adapter transmission device via the first fixed hole, the second fixed hole, and a threaded hole of the adapter transmission device.

10. The adapter according to claim 9, wherein the threaded hole is provided with a first thread;

a first portion of a screw rod of the fixed screw adjacent to a nut of the fixed screw is smooth, and a second portion of the screw rod away from the nut is provided with a second thread matching with the first thread;

an outer diameter of the first portion of the screw rod is smaller than or equal to a minimum inner diameter of the first fixed hole, an outer diameter of the second portion of the screw rod is greater than the minimum inner diameter of the first fixed hole, and the outer diameter of the second portion of the screw rod is smaller than or equal to an inner diameter of the second fixed hole.

11. The adapter according to claim 10, wherein the first fixed hole comprises a first through hole and a second through hole which are axially connected, and the first through hole is provided on a side away from the second fixed hole;

an inner diameter of the first through hole is equal to or larger than the outer diameter of the first portion of the screw rod, the inner diameter of the first through hole is smaller than the outer diameter of the second portion of the screw rod, and an inner diameter of the second through hole is larger than or equal to the outer diameter of the second portion of the screw rod.

12. A surgical assistance system, comprising an adapter transmission device and an adapter according to claim 1, wherein the adapter transmission device is configured to drive the first input shaft and the second input shaft separately.

* * * * *